United States Patent [19]
Barrett et al.

[11] Patent Number: 5,586,564
[45] Date of Patent: Dec. 24, 1996

[54] INSTRUMENTATION AND SURGICAL PROCEDURE FOR DECOMPRESSION FOR MORTON'S NEUROMA

[75] Inventors: Stephen L. Barrett; Michael G. Brown, both of The Woodlands, Tex.

[73] Assignee: Instratek, Inc., Houston, Tex.

[21] Appl. No.: 192,167

[22] Filed: Feb. 4, 1994

[51] Int. Cl.$^6$ .............................. A61B 19/00; A61B 17/32
[52] U.S. Cl. ............................................ 128/898; 606/167
[58] Field of Search ...................... 128/898; 606/167–170

[56] References Cited

U.S. PATENT DOCUMENTS

| | | |
|---|---|---|
| 4,819,620 | 4/1989 | Okutsu . |
| 4,962,770 | 10/1990 | Agee et al. . |
| 5,029,573 | 7/1991 | Chow . |
| 5,253,659 | 10/1993 | McNamara et al. . |
| 5,269,290 | 12/1993 | Barrett et al. . |
| 5,323,765 | 6/1994 | Brown ................................ 606/170 X |
| 5,334,214 | 8/1994 | Putnam .............................. 128/898 X |
| 5,366,465 | 11/1994 | Mirza .................................. 128/898 X |
| 5,392,787 | 2/1995 | Yoon ....................................... 128/898 |

OTHER PUBLICATIONS

Brochure—Linvatec Concept Arthroscopy, The Concept® CTS Relief Kit™ Surgical Technique—Copyright 1992.
Brochure—Acufex®—The Light at the End of Carpal Tunnel Syndrome—Copyright 1992.
Brochure—Davol, Endoscopic Carpel Tunnel Release System—Copyright May, 1993.
Brochure—Agee Carpal Tunnel Release System—Copyright Feb., 1992.
Brochure—An Illustrated Guide to the Modified Chow Technique Endoscopic Release of the Carpal Ligament—Copyright 1992.
Brochure—Instratek Endoscopic Plantar Fasciotomy—Copyright 1992.
Brochure—Instratek Endoscopic Carpal Tunnel Release—Copyright 1992.
Quirk, Morton's neuroma, 1987.
Tate, Rusin, Morton's Neuroma—Its Ultrastructural Anatomy and Biomechanical Etiology, Dec. 1978.
The American College of Foot Surgeons—Intermetatarsal Neuroma, 1992.
Young, Lindsey—Etiology of Symptomatic Recurrent Interdigital Neuromas, May, 1993.
Wachter, Nilson, Thul—The Relationship between Foot Structure and Intermetatarsal Neuromas, Copyright 1984.
Bartolomei, Wertheimer—Intermetatarsal Neuromas: Distribution and Etiologic Factors, 1983.
Finney, Wiener, Catanzariti—Treatment of Morton's Neuroma Using Percutaneous Electrocoagulation, Dec. 1989.
Gauthier, Thomas Morton's Disease: A Nerve Entrapment Syndrome, Dec. 1978.
Johnson, Johnson and Unni—Persistent Pain after Excision of an Interdigital Neuroma, Jun. 1988.
Burns, Stewart—Morton's Neuroma: Preliminary Report on Neurectomy Via Transverse Plantar Incision, Mar. 1982.
Dellon—Treatment of Recurrent Metatarsalgia by Neuroma Resection and Muscle Implantation: Case Report and Proposed Algorithm of Management for Morton's "Neuroma", 1989.

*Primary Examiner*—Michael Powell Buiz
*Assistant Examiner*—Nancy Connolly Mulcare
*Attorney, Agent, or Firm*—Barnes & Thornburg

[57] ABSTRACT

New surgical instrumentation and a new surgical procedure is used for decompression for Morton's neuroma. The patient is prepared for surgery. An incision is made in the dorsal aspect of the foot, another incision is made between the digits of the foot, and then another incision is made on the bottom of the foot. A metatarsal spreader or retractor of the present invention can be inserted through the dorsal incision to spread the metatarsals. A slotted cannula and trocar assembly of the present invention is inserted into the interdigital portal and through the proximal portal. The trocar is removed and an endoscope is inserted into the cannula through the dorsal portal. A lumbrical hook of the present invention is inserted into the proximal portal of the cannula and used to hook the lumbrical tendon. A hook blade is used to sever the intermetatarsal ligament. Once release of the intermetatarsal ligament has been achieved, the instrumentation is removed and a bandage is placed about the foot.

28 Claims, 5 Drawing Sheets

OTHER PUBLICATIONS

Gaynor, Hake, Spinner, Tomczak—A Comparative Analysis of Conservative versus Surgical Treatment of Morton's Neuroma, Jan. 1989.

Alexander, Johnson, Parr—Morton's Neuroma: A Review of Recent Concepts.

Beskin, Baxter—Recurrent Pain Following Interdigital Neurectomy-A Plantar Approach, Aug. 1988.

Turan, Lindgren, Sahlstedt—Computed Tomography for Diagnosis of Morton's Neuroma, Copyright 1991.

Sartoris, Brozinsky, Resnick—Magnetic Resonance Images, Copyright 1989.

Erickson, Canale, Carrera, Johnson, Shereff, Gould, Hyde, Jesmanowicz—Interdigital (Morton) Neuroma: High–Resolution MR Imaging with a Solenoid Coil, 1991.

Redd, Peters, Emery, Branch, Rifkin—Morton Neuroma: Sonographic Evaluation, 1989.

Mulder—The Causative Mechanism in Morton's Metatarsalgia, Feb. 1951.

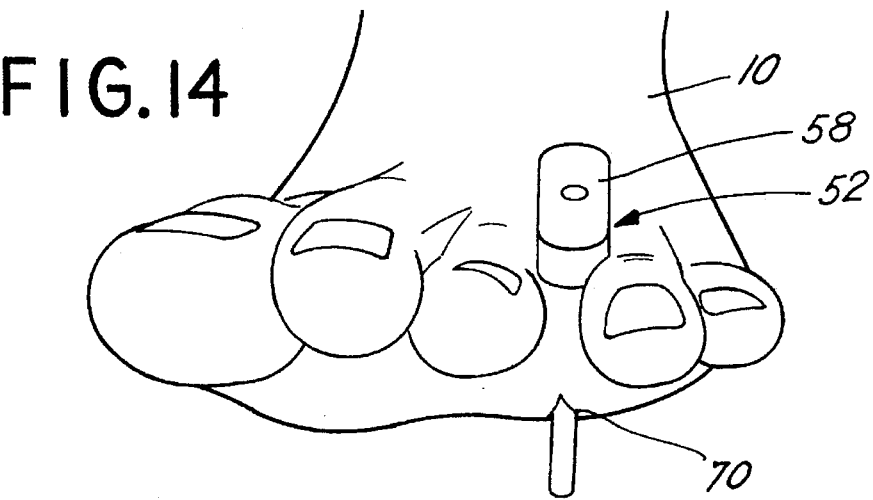
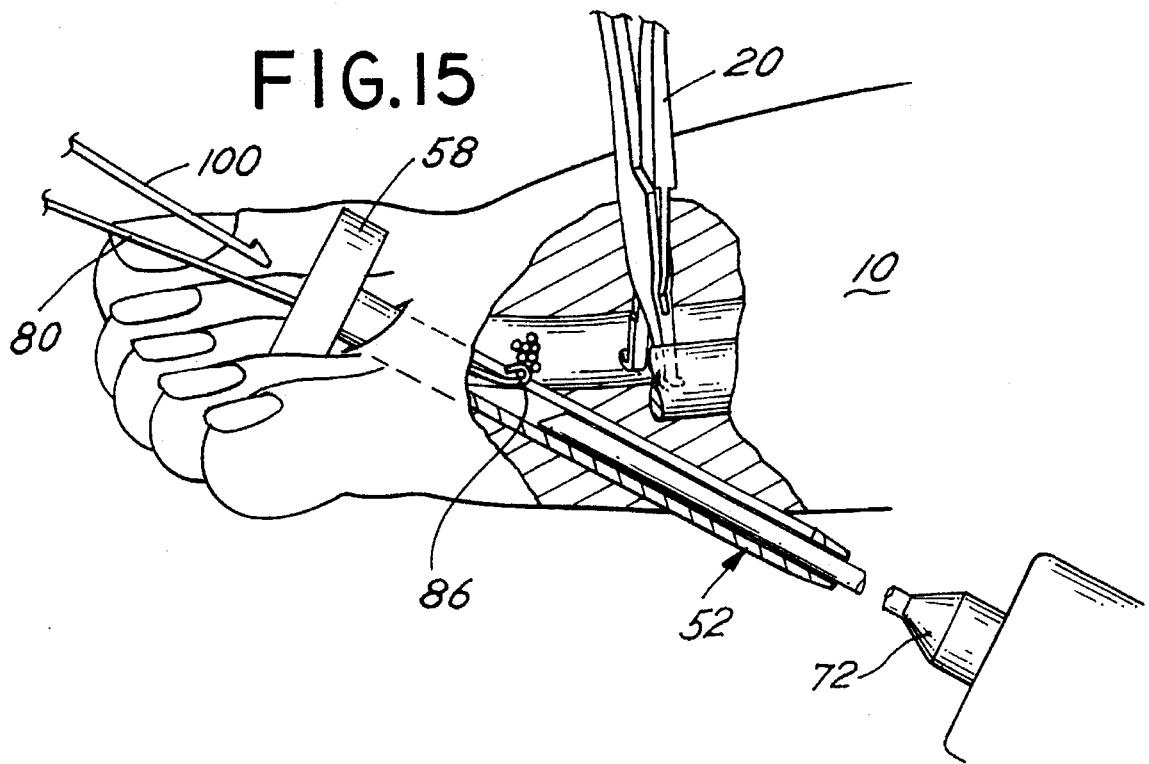

INSTRUMENTATION AND SURGICAL PROCEDURE FOR DECOMPRESSION FOR MORTON'S NEUROMA

BACKGROUND AND SUMMARY OF THE INVENTION

The present invention relates generally to a new podiatric surgical procedure and instrumentation. More particularly, the present invention relates to instrumentation and a surgical procedure for endoscopic decompression for Morton's neuroma.

Morton's neuroma is a frequent foot disorder that affects a significant percentage of the people in the United States. Morton's neuroma is a swelling at the bifurcation of one of the digital branches of the plantar nerves. The most common site is in the third intermetatarsal space. Morton's neuromas are also found in the second intermetatarsal space and fourth intermetatarsal space, and rarely in the first intermetatarsal space. In a typical case, the patient experiences sharp pain at the base of the toes, which sometimes radiates into the toes. There can be proximal radiation as well, even as far as the shin. The pain is sometimes described as a burning or "electric shock" sensation. Occasionally, numbness or hyperaesthesia in the toes is present.

The term "neuroma" may actually be a misnomer. Although intermetatarsal neuromas may resemble amputation or "stump" neuromas, the two are different from a histological perspective. Intermetatarsal neuromas are typically characterized by degenerative changes, such as demyelination and wallerian degeneration. Stump neuromas are typically characterized by proliferative changes.

The etiology of Morton's neuroma has been debated in medical literature. T. G. Morton believed that Morton's neuroma was caused by an abnormal metatarsal parabola, a result of pinching of the digital nerves by the metatarsal heads. Betts attributed the cause of the third intermetatarsal neuroma to the fact that the common digital nerve in that interspace received branches from both the medial plantar nerve and the lateral plantar nerve, resulting in a thicker nerve. Nissen felt that the etiology was related to ischemia of the involved nerve. Bossley described the symptoms to be related to inflammation of an intermetatarsal bursa. Gibney believed it to be secondary to flatfoot, while Wachter described how pes cavus feet have an increased incidence of neuromas because of increased tension in the plantar fascia and intermetatarsal ligaments.

Recent evidence points to chronic intermittent trauma being caused by compression and stretching of the common digital nerve. It appears that the transverse intermetatarsal ligament plays a role in this theory. Ground reaction forces create impingement of the neurovascular bundle between the metatarsal heads, because the transverse intermetatarsal ligament does not allow the nerve to move dorsally. Stretching of the nerves occurs during propulsion, as dorsiflexion of the digits stretches it around the rigid intermetatarsal ligament. Graham confirmed this by noting that the characteristic degenerative changes of the nerve occurred just distal to the distal edge of the transverse intermetatarsal ligament.

Treatment of Morton's neuroma has also been the subject of much debate. Various non-invasive conservative care techniques have been tried, such as non-steroidal anti-inflammatory agents, injections of local anesthetics, corticosteroids, orthotic management, padding, strapping and others. However, success with such non-invasive care has been limited.

The medical field has generally adopted two surgical approaches for relieving the pain associated with Morton's neuroma. The first and most common technique consists of resection of the common digital nerve. This procedure can lead to loss of function of the involved nerve and true "stump" neuroma formation. While this type of surgical intervention has a success rate approaching 80%, in some cases the stump neuroma becomes symptomatic post-operatively. This can result in the patient realizing symptoms of pain which are equal, or sometimes worse, than the pain experienced prior to the surgical intervention.

The second approach consists of decompression of the common digital nerve. In mild cases where symptoms are intermittent, the patient is treated by modifying the patient's activities and orthotics. Moderate cases are treated by division of the intermetatarsal ligament through a dorsal approach. Severe cases may add a microsurgical internal neurolysis of the common digital nerve. If pain recurs, treatment for the first recurrence may include a resection of the nerve through a dorsal approach. If a second recurrence occurs, then further resection through a plantar incision and implantation of the proximal aspect of the nerve into muscle may be performed.

Under either of these two surgical techniques, a relatively large incision is made in the foot. The patient typically spends approximately two weeks in a post-operative surgical shoe until sutures are removed. Typically, the patient requires six-eight weeks to become fully ambulatory in normal day-to-day athletic and non-athletic activities.

Accordingly, it is an object of the present invention to provide surgical instrumentation and a surgical procedure to relieve the pain associated with Morton's neuroma and which minimizes the length of time necessary for patient recovery and resumption of normal activities.

Another object of the present invention is to provide surgical instrumentation and a surgical procedure to relieve the pain associated with Morton's neuroma which minimizes the surgical trauma incident to treatment of Morton's neuroma disorder.

These and other objects are attained by the provision of surgical instrumentation and a surgical procedure for relieving the pain associated with Morton's neuroma. First, the patient is prepared and draped in the usual aseptic manner.

Three portal incisions are made. A dorsal incision is made between the metatarsals of the affected interspace on the dorsal aspect of the foot. An interdigital incision is then made between the digits in the interdigital space. Next, a pair of blunt dissecting scissors are inserted into the dorsal incision, and dissection is performed percutaneously between the metatarsal heads. The dissecting scissors are removed, and the metatarsal spreader of the present invention is introduced into the dorsal portal between the metatarsal heads. A small interosseus elevator is then introduced into the interdigital incision to palpate the intermetatarsal ligament from the interdigital portal incision.

The elevator is then placed proximally along the course of the intermetatarsal ligament, inferior, parallel and longitudinal to the direction of the metatarsals, via the interdigital incision. The elevator can then be palpated percutaneously on the plantar aspect of the patient's arch. After the elevator is removed from the interdigital portal incision, a slotted cannula and trocar is introduced through the interdigital incision and into the channel created by the elevator. A proximal incision is made in the proximal aspect of the foot, allowing passage of the cannula and trocar through the skin of the plantar aspect of the foot. The cannula is left in place and the trocar is withdrawn from the slotted cannula. Cotton-tipped applicators can be placed through the cannula in order to remove any adipose tissue which is in the cannula.

The cannula and trocar assembly of the present invention includes a slotted cannula and a trocar. The slotted cannula includes a head at one end, which abuts the handle portion of the trocar. The trocar handle includes a tapered, elongated neck. The head of the cannula is similar in shape to the neck of the trocar and allows the trocar and cannula assembly to be positioned between the digits of the foot.

Next, an endoscope is placed in the proximal portal of the slotted cannula, which allows visualization of the intermetatarsal ligament, as well as the lumbrical tendon. A lumbrical hook is then inserted into the distal portal of the cannula. The lumbrical hook of the present invention includes a handle and an insert which is releasably secured by the handle. The insert includes a bend at one end which enables the insert to be secured within the handle. Opposite the bend, the insert includes a hook, which can be used to engage the lumbrical tendon. Using the hook, the lumbrical tendon is brought to one side of the slotted cannula, exposing complete visualization of the intermetatarsal ligament. A hook knife is then used to engage the intermetatarsal ligament from proximal, and a retrograde motion at the distal end of the cannula allows for severance of the intermetatarsal ligament.

The endoscope can be removed and placed in the distal portal of the cannula, allowing visualization of the proximal aspect of the intermetatarsal ligament. If there are any remaining fibers, these are then released using the hook blade. At this time, complete visualization of the severance of the ligament may be achieved, assuring completion of the surgery. The slotted cannula is copiously lavaged with sterile saline to remove any cotton fibers left behind.

Prior to closing the incisions, the intermetatarsal elevator can be placed into the interdigital portal incision, and allowed to pass between the metatarsal heads freely without impedance by the intermetatarsal ligament. This assures that a complete release of the intermetatarsal ligament has been achieved. The portal incisions are then closed in a standard manner. A sterile compressive gauze dressing is then placed on the patient. The patient is allowed to ambulate immediately.

Other objects, advantages and novel features of the present invention will become apparent from the following detailed description of the invention when considered in conjunction with the accompanying drawings.

BRIEF DESCRIPTION OF THE DRAWINGS

FIG. 14 is a front view of the foot showing the cannula of the present invention therethrough.

FIG. 15 is a side view of the foot, showing portions of the anatomy of the foot as well as the positioning of the cannula and the retractor of the present invention.

DETAILED DESCRIPTION OF THE PREFERRED EMBODIMENTS

Figure 1:
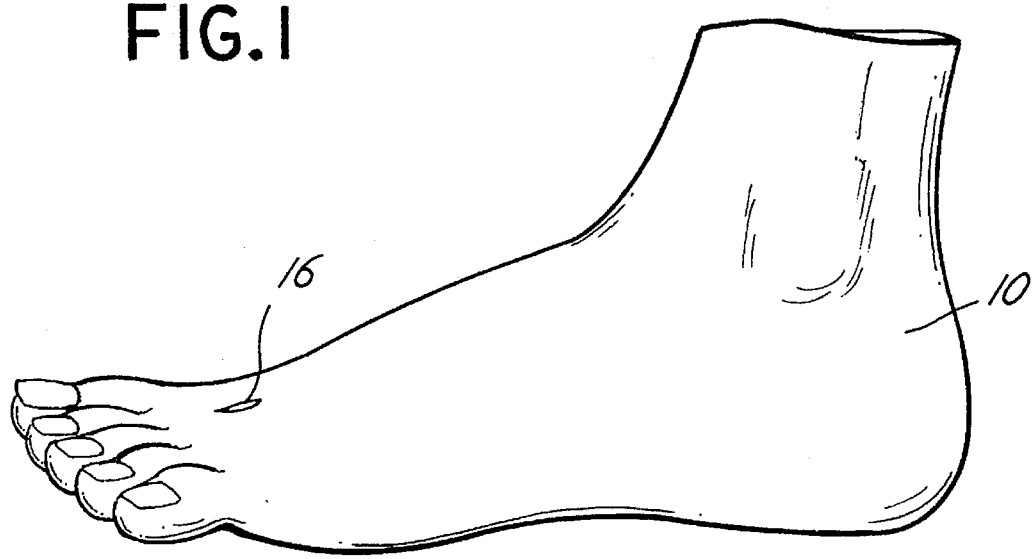
FIG. 1 is a side view of a foot showing the dorsal incision of the present invention.
Figure 2:
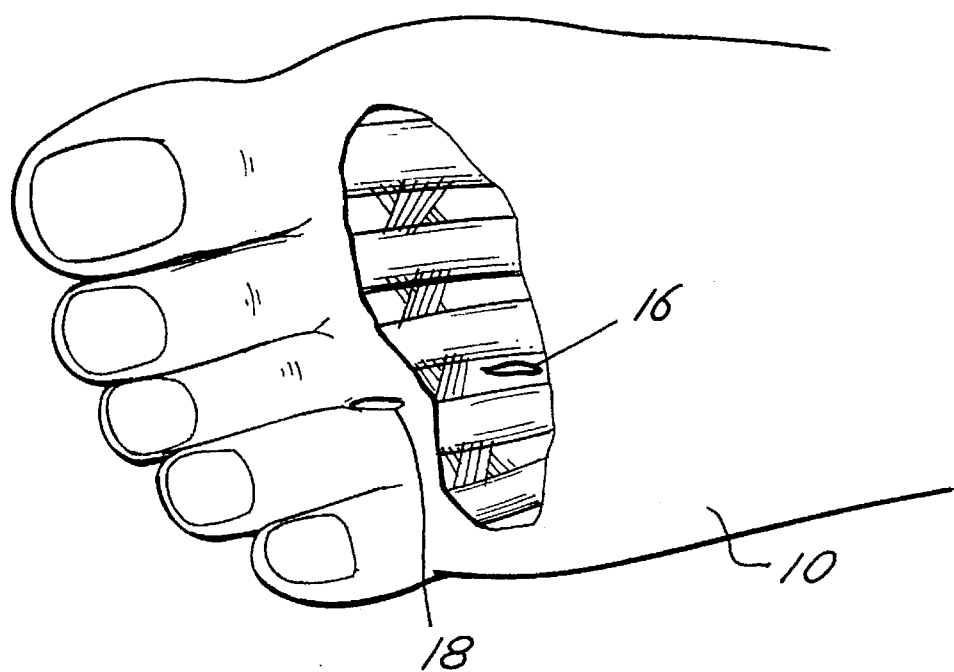
FIG. 2 is a top view of a foot, showing portions of the anatomy of the foot.

Referring now to the drawings, in which like-referenced characters indicate corresponding elements throughout the several views, attention is first directed to FIG. 1. Foot 10 includes a plurality of digital nerves extending therethrough. Foot 10 also includes the transverse intermetatarsal ligament which extends generally transverse to the nerves. It is believed that Morton's neuroma is caused by the stretching of the nerves around the intermetatarsal ligament. The instrumentation and procedure of the present invention allows a surgeon to sever or cut the transverse metatarsal ligament, thereby relieving the patient of the pain caused by the neuroma.

Because of the minimal invasiveness of the procedure, local anesthesia can be used. Local anesthesia also allows the patient to become ambulatory soon after the operation. Furthermore, because the procedure of the present invention is a minimally traumatic procedure, the exposure to higher risks associated with other anesthetics may not be needed. In addition, local anesthesia can be more cost effective than other forms of anesthesia. One method of anesthetizing the foot includes the use of 1:1 ratio of 0.5% Marcaine plain, mixed with 2% Lidocaine plain. Nerve blocks to be achieved include the deep peroneal, superficial peroneal and posterior tibial nerve.

Using a skin marker, anatomical reference points are mapped out on the foot. The reference points needed may be dependant upon the location of the neuroma. Typically, the second, third and fourth metatarsals and metatarsophalangeal joints may be mapped out dorsally. Also, the heads of the second, third, and fourth metatarsals may be mapped out plantarly.

Next, the foot may be exsanguinated with an esmark bandage. The foot is then placed in an inflatable ankle tourniquet, and the tourniquet is inflated to approximately 250 millimeters of mercury of pressure.

After having prepared the patient for surgery, a dorsal incision 16 can be made. The dorsal incision 16 is made between the metatarsals of the affected interspace on the dorsal aspect of foot 10. As shown, dorsal incision 16 is made in a longitudinal manner, proximal to and between the metatarsal heads. Dorsal incision 16 can be a small stab incision, approximately 5 millimeters in length. Various types of instrumentation may be used, and those referenced generally are described for illustrative purposes only. For example, dorsal incision 16 may be made with a number 15 blade.

Next, an interdigital incision 18 may be made between the digits in the interdigital space or web space adjacent the affected interspace, for example, between the third and fourth digits. Interdigital incision 18 can also be a small stab incision, and is made in a transverse or horizontal manner. Next, blunt dissection can be performed percutaneously between the metatarsal heads. This can be performed with a small pair of blunt dissecting scissors. This separates the surrounding adipose tissue from the portal tracts. Next, a metatarsal spreader or retractor 20 may be introduced into the dorsal portal between the metatarsal heads. The metatarsal spreader 20 can be locked open, causing distraction of the metatarsals. This results in tension across the intermetatarsal ligament.

Metatarsal spreader 20 of the present invention is shown in FIGS. 3–12. Metatarsal spreader 20 includes opposing legs 22, which operate in a scissor-like manner. At one end of each leg 22 is an opening means, such as finger hole 24. At the opposite end of each leg 22 is jaw 26. Legs 22 are hingedly attached, such that opening or expanding finger holes 24 cause jaws 26 to open, or spread apart. It is jaws 26 which contact or engage the metatarsals during use.

Adjacent finger holes 24, metatarsal spreader 20 includes a locking mechanism. Wire 28 is fixably attached to one leg 22, and is slidably disposed within cylinder 30, mounted to the opposite leg 22. Cylinder 30 is internally threaded, and includes screw 32. As finger holes 24 are spread apart, wire 28 slides within cylinder 30. When the metatarsal spreader 20 is in a desired position, screw 32 may be tightened, thus securing wire 28 to cylinder 30. This effectively locks metatarsal spreader 20 in position.

Each jaw 26 includes tooth 34 thereon. Tooth 34 extends generally orthogonally from the foot, in an outward direction. Tooth 34 is tapered to distal point 36. Thus, tooth 34 has a generally triangular configuration. Point 36 allows jaw 26 to grip the metatarsals.

Figure 7:
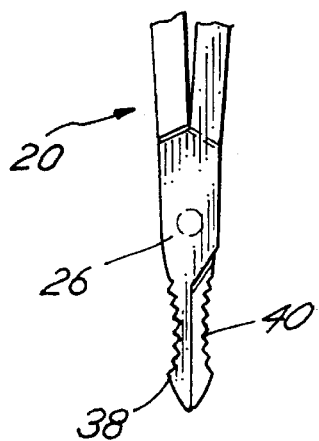
FIG. 7 is a front view of the jaws of another embodiment of the retractor of the present invention.
Figure 8:
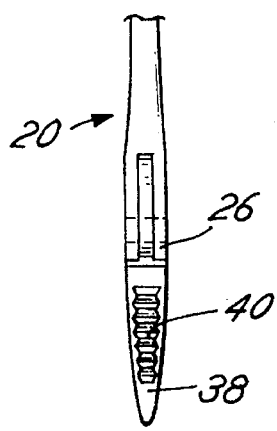
FIG. 8 is a side view of the jaws of the retractor shown in FIG. 7.
Figure 9:
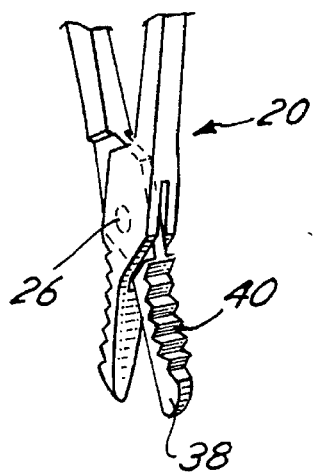
FIG. 9 is a perspective view of the jaws of the retractor shown in FIG. 7.

Another embodiment of metatarsal spreader 20 of the present invention is shown in FIGS. 7–9. In this embodiment, tooth 34 on jaw 26 is replaced by gripper 38. Gripper 38 is a curved member, in a concave manner. Gripper 38 is substantially crescent-shaped, and may be connected to jaw 26 at an angle. Gripper 38 may also include serrated surface 40. Serrated surface 40 includes a plurality of points along the concave surface of gripper 38. Serrated surface 40 contacts and grips the metatarsal during distraction.

Figure 10:
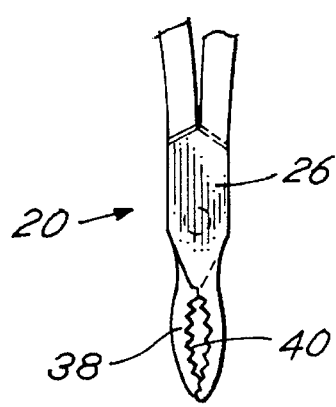
FIG. 10 is a front view of the jaw portion of another embodiment of the retractor of the present invention.
Figure 11:
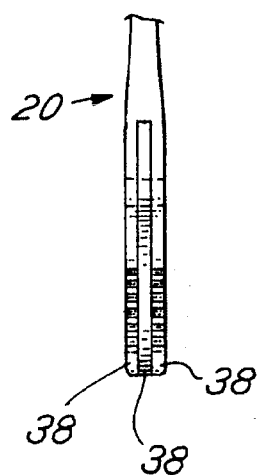
FIG. 11 is a side view of the jaws of the retractor shown in FIG. 10.
Figure 12:
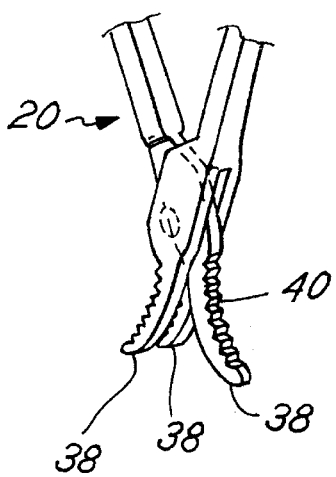
FIG. 12 is a perspective view of the jaws of the retractor shown in FIG. 10.

Another embodiment of metatarsal spreader 20 is shown in FIGS. 10–12. In this embodiment, retractor 20 includes 3 grippers 38, spaced in an overlapping or interleaf fashion. Two grippers 38 are attached to one jaw 26, and one gripper 38 is attached to the opposite jaw. In a closed position, the single gripper rests substantially between the opposing two grippers. This embodiment may be used with either gripper 38 or tabs 34.

Each of the embodiments of metatarsal spreader 20 is used in substantially the same manner. Finger holes 24 are pushed together, so that the spreader is in a closed position. The jaws are then inserted through dorsal incision 16 such that tabs 34 or grippers 38 are substantially parallel to the metatarsal. After jaws 26 have been inserted into the foot, metatarsal spreader 20 is rotated through an angle of approximately 90 degrees. In this position, point 36 of tooth 34 or the serrated surface 40 of gripper 38 contacts the opposing metatarsals. Finger holes 24 are then spread apart, causing the jaws to exert pressure on the metatarsals. Finger holes 24 are opened until the metatarsals are distracted a desired amount. Screw 32 is then tightened securing wire 28, and locking metatarsal spreader 20 in position.

A small interosseus elevator can then be used to palpate the intermetatarsal ligament from the interdigital portal incision. The elevator can then be placed proximally along the course of the intermetatarsal ligament parallel and longitudinal to the direction of the metatarsals. The elevator can then be palpated percutaneously on the plantar aspect of the patient's arch.

After removing the elevator from the interdigital portal, trocar and cannula assembly 50 is introduced into the channel created by the elevator, through interdigital incision 18. Trocar and cannula assembly 50 of the present invention includes slotted cannula 52 and trocar 54. Cannula 52 is a generally hollow tubular member. Cannula 52 includes a slot 56 therein, disposed in a generally longitudinal manner in the cannula. Cannula 52 also includes head 58. Head 58 is disposed at one end of cannula 52 and is also generally hollow.

Figure 13:
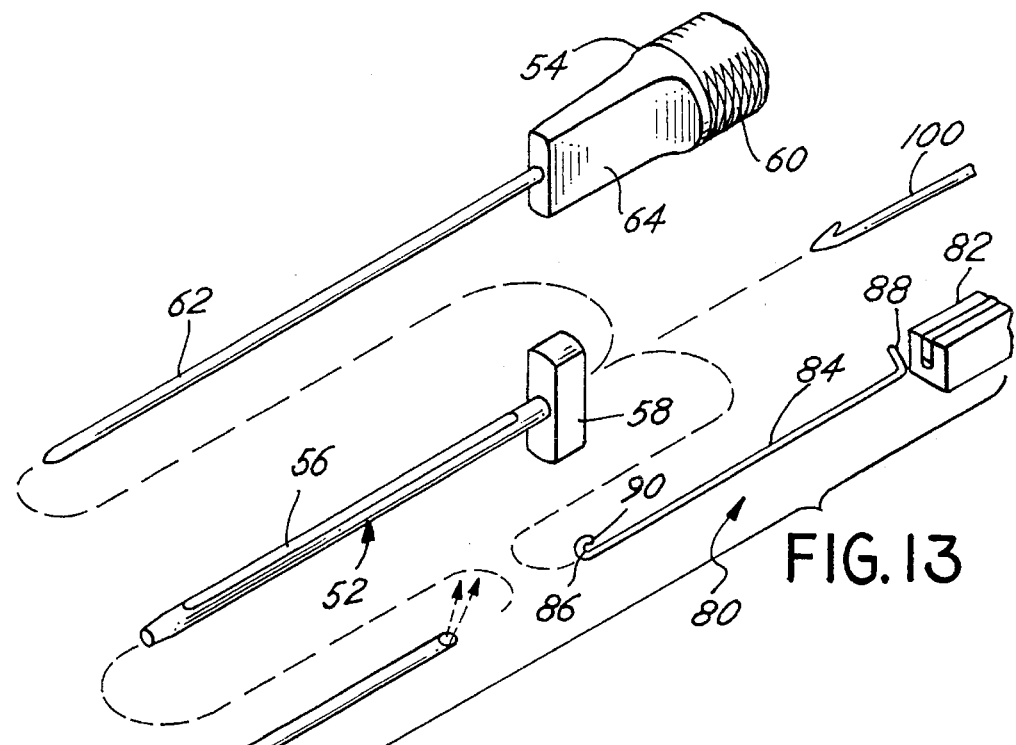
FIG. 13 is a perspective view of the trocar and cannula assembly and lumbrical hook of the present invention, as well as other instrumentation.
Figure 3:
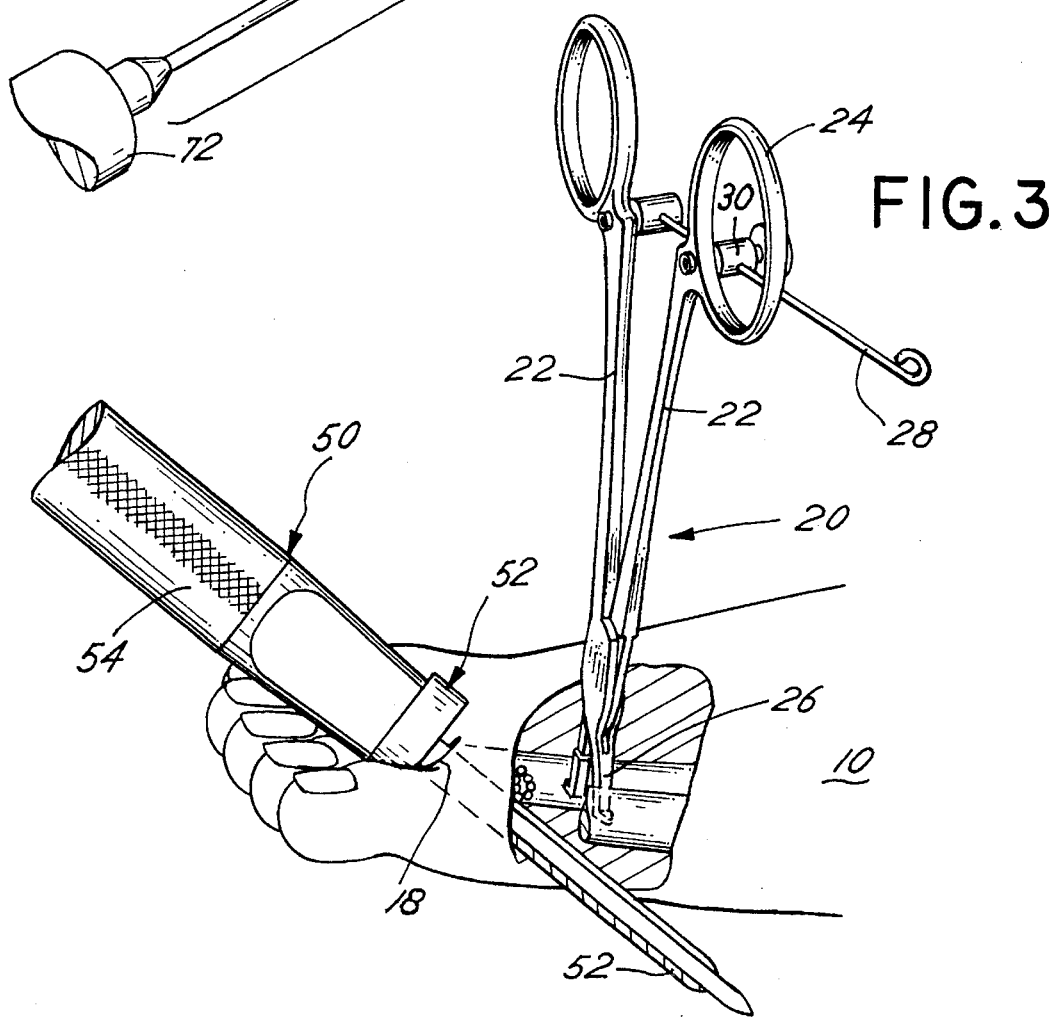
FIG. 3 is a side view of a foot, showing the placement of the trocar and cannula assembly and retractor of the present invention.
Figure 4:
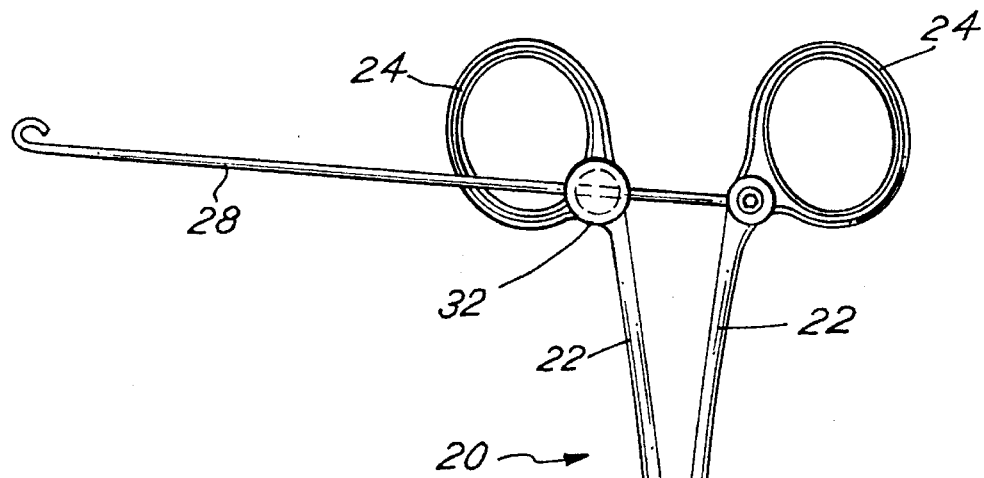
FIG. 4 is a front view of a retractor of the present invention.
Figure 5:
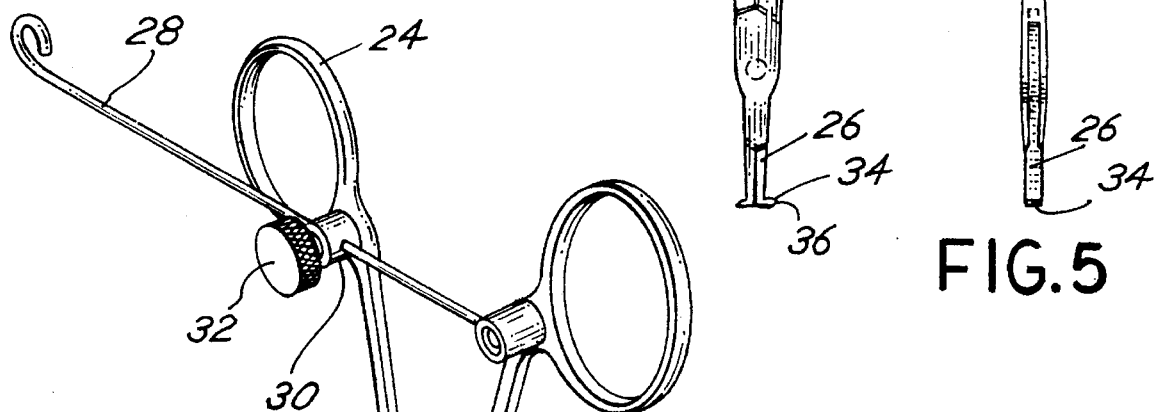
FIG. 5 is a side view of the jaws of the retractor shown in FIG. 4.
Figure 6:
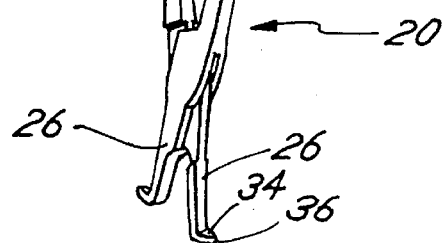
FIG. 6 is a perspective view of the retractor shown in FIG. 4.

Trocar 54 generally includes handle 60 and rod 62. As can be seen in FIG. 13 cannula 52 may be positioned in a slidable relationship over rod 62, such that head 58 abuts handle 60. Handle 60 is shown being of a generally cylindrical shape. However, the shape of handle 60 may be varied.

Handle 60 includes neck 64. Neck 64 is tapered such that it has a generally narrow, elongated cross section. As shown, the width of neck 64 is less than the width of handle 60. Neck 64 has a width dimension which is substantially the same as the width dimension of head 50 of cannula 52. However, the longitudinal dimension of head 58 is slightly larger than the longitudinal dimension of neck 64. This allows a user to grasp or push on head 58 while removing trocar 54 from cannula 52. The slender aspect of head 58 and neck 64 allow trocar and cannula assembly 50 to be positioned in the interdigital space between the toes of foot 10.

The cannula and trocar assembly 50 is placed inferior to the intermetatarsal ligament via palpation of the tip of the trocar percutaneously in the patient's arch. Slot 56 of cannula 52 is positioned to allow access to the intermetatarsal ligament. A proximal incision 70 is made in the plantar aspect of foot 10, allowing the cannula and trocar assembly 50 to pass through foot 10. As shown, proximal incision 70 is approximately 4–5 millimeters in length. Having substantially pierced the foot with trocar and cannula assembly 50, trocar 54 is then removed from cannula 52, leaving the cannula in juxtaposition to the intermetatarsal ligament, inferior to the ligament. Cotton-tipped applicators can then be placed through cannula 52 in order to remove any adipose tissue which is in the cannula.

Next, endoscope 72 is placed in cannula 52 to allow visualization of the intermetatarsal ligament. Endoscope 72 may be placed in the proximal portal of the slotted cannula, through the interdigital incision 18. Although various types of instrumentation may be used, one such endoscope 72 is a 2.7 millimeter, 30-degree beveled endoscope. Introducing endoscope 72 into cannula 52 allows visualization of the transverse intermetatarsal ligament. This scope can be coupled to a two-camera system with compatible light source, thus providing image on a high resolution medical grade television monitor, such as the 25 inch resolution medical grade television monitor manufactured by Sony Corporation. In addition, a quality VHS format video recorder can provide hard copy, real time documentation of the procedure. Quite often, the lumbrical tendon may also be visualized.

Next, lumbrical hook 80 may be introduced into the distal portal of cannula 52, through proximal incision 70. Lumbrical hook 80 of the present invention generally comprises two elements: handle 82 and insert 84. Handle 82 includes a releasable locking mechanism, which allows insert 84 to be locked in place within handle 82 and also quickly released and removed from the handle. Insert 84 is a slender, elongated member. Insert 84 includes hook 86 at one end and bend 88 at its opposite end. Bend 88 is an engagement means which engages the lock mechanism of handle 82, such that the insert is secured by the handle. Hook 86 includes opening 90 therein. Hook 86 is designed to be able to engage the lumbrical tendon by "hooking" the tendon within hook 86.

The lumbrical tendon is manipulated within hook 86 and drawn towards one side of slotted cannula 52, thereby exposing complete visualization of the intermetatarsal ligament. Use of lumbrical hook 80 may be advantageous, allowing for careful palpation of the area for any neurovascular structures, so that they may be identified and avoided. Using a cutting instrument such as hook blade 100, the intermetatarsal ligament may then be engaged from proximal. Using a retrograde motion at the distal end of cannula 52 allows for severance of the intermetatarsal ligament. Typically, several passes may be made with hook knife 100 to sever the ligament. The edges of the intermetatarsal ligament can typically be seen during resection; however, occasionally, further retraction of the intermetatarsal retractor is needed to visualize the edges of the ligament. Care should be used when severing the intermetatarsal ligament, so that there is no damage done to the lumbrical tendon, or other surrounding neurovascular structures.

Occasionally, a few fibers of the intermetatarsal ligament remain proximally, and can be released from the proximal end of cannula 52. At this time, endoscope 72 and lumbrical hook 80 can be removed from the cannula, and inserted into the opposite portals of the cannula, allowing visualization of the proximal aspect of the intermetatarsal ligament. If any fibers remain, hook knife 100 can be inserted into the proximal portal of cannula 52 to release the remaining fibers. At this time, complete visualization of the severance of the intermetatarsal ligament can be achieved.

Next, cannula 52 is lavaged with sterile saline to remove any cotton fiber that may be left behind from the cotton-tipped applicator. The instrumentation is then removed from the foot.

Prior to closing the incisions, the intermetatarsal elevator may be placed into the interdigital portal incision 18, and allowed to pass between the metatarsal heads freely without impedance by the intermetatarsal ligament. This provides further assurance that complete release of the intermetatarsal ligament has been achieved, and that no fibers remain intact. The portal incisions are then closed in a standard manner, such as with simple interrupted sutures. A sterile compressive gauze dressing is placed on the patient. The patient may ambulate soon after surgery.

Although the present invention has been described in detail, the same is by way of illustration and example only and is not to be taken as a limitation of the present invention. The scope of the present invention is defined only by the terms of the appended claims. For example, it may be possible to maintain the effectiveness of the surgical procedure of the present invention without performing each and every step of the procedure. The procedure described in detail is designed to provide maximum efficiency and success, while minimizing patient trauma.

However, it may be possible to relieve the symptoms of Morton's neuroma through a procedure which does not include each and every step outlined above. The additional steps cited herein may be helpful in reducing the trauma and pain experienced by the patient, as well as assisting the surgeon in ensuring a complete release of the intermetatarsal ligament has been achieved, while reducing the likelihood of damage to other surrounding neurovascular tissue.

What is claimed is:

1. A surgical method for decompressing Morton's neuroma, comprising the steps of:
   making a first incision in a foot;
   introducing an elevator into the first incision to palpate the intermetatarsal ligament;
   inserting a cannula into the first incision;
   making a second incision in the foot;
   projecting the cannula through the second incision;
   inserting an endoscope into the cannula to allow projected viewing of the anatomy of the foot;
   inserting a cutting instrument into the cannula; and
   manipulating the cutting instrument to sever the intermetatarsal ligament.

2. The method according to claim 1 including the step of marking coordinates on the foot prior to making the first incision.

3. The method according to claim 1 including the step of anesthetizing the foot prior to making the first incision.

4. The method according to claim 1 including the step of exsanguinating the foot prior to making the first incision.

5. The method according to claim 1 wherein the first incision is made between the digits adjacent the affected interspace.

6. The method according to claim 1 wherein the cannula includes a trocar therein.

7. The method according to claim 6 including the step of removing the trocar from the cannula prior to inserting the endoscope into the cannula.

8. The method according to claim 1 wherein the second incision is made in the plantar aspect of the foot.

9. The method according to claim 1 wherein the cutting instrument is a hook knife.

10. The method according to claim 1 wherein the cutting instrument is manipulated from proximal in a substantially retrograde motion.

11. The method according to claim 1 wherein the first incision is a stab incision.

12. The method according to claim 1 further including the step of dissecting between the metatarsal heads of the affected interspace prior to inserting the cannula into the first incision.

13. The method according to claim 1 further including the step of making an incision in the dorsal aspect of the foot prior to making the first incision.

14. The method according to claim 13 further including the step of introducing a metatarsal distractor into the dorsal incision prior to inserting the cannula into the first incision.

15. The method according to claim 1 further including the step of inserting an elevator into the first incision to palpate percutaneously the plantar aspect of the patient's arch.

16. The method according to claim 15, further including the step of removing the elevator from the first incision prior to inserting the cannula into the first incision.

17. The method according to claim 1 including the step of removing any adipose tissue in the cannula prior to inserting the endoscope into the cannula.

18. The method according to claim 1 further including the step of hooking the lumbrical tendon with a lumbrical hook and manipulating the tendon toward the cannula prior to manipulating the cutting instrument to sever the intermetatarsal ligament.

19. The method according to claim 1 wherein the endoscope is inserted into the cannula through the first incision in the foot.

20. The method according to claim 1 further including the step of removing the endoscope and the cutting instrument from the cannula, and placing the endoscope into the cannula through the second incision and inserting the cutting instrument into the cannula through the first incision, after the step of manipulating the cutting instrument to sever the intermetatarsal ligament.

21. The method according to claim 20, further including the step of manipulating the cutting instrument to sever any remaining fibers of the intermetatarsal ligament.

22. The method according to claim 1 further including the step of removing the cutting instrument and the endoscope from the cannula after manipulating the cutting instrument to sever the intermetatarsal ligament.

23. The method according to claim 1 further including the step of lavaging the cannula with sterile saline.

24. The method according to claim 1 further including the step of inserting an intermetatarsal elevator into the first incision to insure no impedance by the intermetatarsal ligament.

25. The method according to claim 1 further including the step of removing all instrumentation from the foot.

26. The method according to claim 25 further including the step of closing all incisions.

27. The method according to claim 26 further including the step of placing a sterile compressive gauze dressing on the patient.

28. A surgical method for decompression for Morton's neuroma, comprising the steps of:

preparing the patient for surgery;

making a first incision in the patient's foot;

making a second incision in the foot;

dissecting between the metatarsal heads;

palpating the intermetatarsal ligament;

palpating the plantar aspect of the patient's arch;

inserting a cannula and trocar into the foot through the second incision;

making a third incision in the foot;

projecting the cannula and trocar through the third incision;

removing any adipose tissue which is in the cannula;

inserting an endoscope into the cannula;

inserting a cutting instrument into the cannula; and manipulating the cutting instrument to sever the intermetatarsal ligament.

* * * * *